(12) United States Patent
Wang et al.

(10) Patent No.: US 9,345,678 B2
(45) Date of Patent: May 24, 2016

(54) PROSTANOID RECEPTOR AGONIST COMPOUNDS AND METHODS OF USE FOR SAME

(71) Applicant: ALLERGAN, INC., Irvine, CA (US)

(72) Inventors: Jenny W. Wang, Irvine, CA (US); David F. Woodward, Lake Forest, CA (US); Neil J. Poloso, Lake Forest, CA (US); Julia Herrmann, Costa Mesa, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/204,845

(22) Filed: Mar. 11, 2014

(65) Prior Publication Data

US 2014/0275266 A1    Sep. 18, 2014

Related U.S. Application Data

(60) Provisional application No. 61/780,594, filed on Mar. 13, 2013.

(51) Int. Cl.
*A61K 31/191* (2006.01)
*A61K 31/557* (2006.01)

(52) U.S. Cl.
CPC ............. *A61K 31/191* (2013.01); *A61K 31/557* (2013.01)

(58) Field of Classification Search
CPC .................................................. A61K 31/5578
See application file for complete search history.

(56) References Cited

U.S. PATENT DOCUMENTS

| 5,093,325 | A | * | 3/1992 | Witt et al. ................... 514/165 |
| 5,506,265 | A | * | 4/1996 | Blitstein-Willinger ....... 514/573 |
| 5,679,707 | A | * | 10/1997 | Okumura et al. ............. 514/468 |
| 5,852,050 | A | * | 12/1998 | Okumura et al. ............. 514/468 |
| 2011/0159073 | A1 | | 6/2011 | Dejuan et al. | |

FOREIGN PATENT DOCUMENTS

| DE | 4124695 A1 | 1/1993 |
| EP | 0583482 A1 | 2/1994 |
| WO | 2005032470 A2 | 4/2005 |

OTHER PUBLICATIONS

Ueda et al. Prostaglandins, leukotrienes, and essential fatty acids (Sep. 1997) vol. 57, No. 3, pp. 285-91.*
Sobolewski et al. Am. J. Physiol. Lung Cell Mol. Physiol., 2004, vol. 287, pp. L352-L359.*
Zhou Weison et al., Prostaglandin I-2 analogs inhibit Th1 and Th2 effector cytokine production by CD4 Tcells, Journal of Leukocyte Biology, Mar. 2007, pp. 809-817, vol. 81, No. 3.
Hatane T. et al., Prostaglandin I2 analog enhances the expression of urokinase-type plasminogen activator and wound healing in cultured human fibroblast, Biochimica Et Biophysica Acta—Molecular Cell Research, Jun. 22, 1998, pp. 189-198, vol. 1403, No. 2.
Journal of Medicinal Chemistry, American Chemical Society, Mar. 1986, pp. 313-315, vol. 29, No. 3.

* cited by examiner

*Primary Examiner* — James D Anderson
(74) *Attorney, Agent, or Firm* — Jonathan Bass

(57) ABSTRACT

Embodiments described herein are directed to prostanoid (IP) receptor agonist compounds, including cicaprost and certain prodrugs, and methods of preparation and use for the same. Certain embodiments are directed to the use of cicaprost and certain prodrugs in the treatment of topical and ocular conditions.

2 Claims, 12 Drawing Sheets

IP Agonist on VEGF Secretion From TNFα-Induced Human Macrophages

PROSTANOID RECEPTOR AGONIST COMPOUNDS AND METHODS OF USE FOR SAME

This application claims the benefit of U.S. Provisional Patent Application Ser. No. 61/780,594, filed Mar. 13, 2013, the entire disclosure of which is incorporated herein by reference.

BACKGROUND OF THE INVENTION

1. Field of the Invention

Embodiments of the present invention are directed to compounds, compositions, formulations, methods, and kits for use as prostanoid receptor agonists, in particular prostanoid IP receptors. Compounds that may be used include cicaprost and other prodrugs thereof, and will be described in greater detail below. The embodiments described herein may be used as agonists to prostanoid IP receptors, and may be useful in treating inflammation, healing wounds, and reducing scar formation.

2. Description of Related Art

Prostanoid receptors, such as the prostanoid IP receptor, are typically G protein-coupled receptors. They may be found on the cell membrane of various cells, and in conjunction with prostanoids (especially prostaglandins and prostacyclins), play important roles in modulating the inflammatory response, among other roles.

Because prostacyclin has a short half-life in the body, analogs have been developed that are inactivated more slowly while still maintaining activity. One of these analogs is cicaprost. The synthesis of cicaprost has been described by Skuballa et al. in "Synthesis of a new chemically and metabolically stable prostacyclin analogue with high and long-lasting oral activity," *J. med. Chem.*, 29, 313-316 (1986), and is hereby incorporated by reference.

BRIEF SUMMARY OF INVENTION

In a preferred embodiment, there is provided a method of activating an IP receptor, wherein the method comprises administering a compound of the formula represented by Formula C, its enantiomers, diastereoisomers, tautomers, hydrates, solvates or a pharmaceutically acceptable salt thereof,

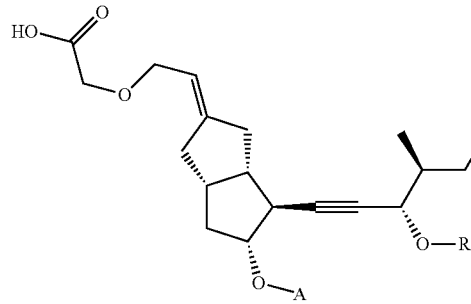

Formula C wherein:
A is selected from the group consisting of hydrogen, acetyl, and —$COCH_2CH_3$; and,
R is selected from the group consisting of hydrogen, acetyl, and —$COCH_2CH_3$.

In some embodiments, the compound is cicaprost. The cicaprost may be administered at a concentration of about 0.1 nM to about 1000 nM. The cicaprost may be administered at a concentration of about 0.001% to about 1%, preferably about 0.1%. In some embodiments, the compound may be administered to a mammal in an amount sufficient to provide a beneficial therapeutic result, wherein the beneficial therapeutic result is selected from the group consisting of reducing inflammation, promoting wound healing, and reducing scarring. In some embodiments, the compound is administered to a mammal in an amount sufficient to at least partially inhibit the production or secretion of inflammatory cytokines and chemokines. In some embodiments, the compound is administered to a mammal in an amount sufficient to at least partially inhibit or reduce the production of at least one selected from the group consisting of IL-8, MCP-1, MIP-1α, MIP-1β, RANTES, and TNF-α. In some embodiments, the compound is administered to a mammal in an amount sufficient to stimulate the production or secretion of VEGF. The compound may be administered to the eye of a mammal. In some embodiments, administration of the compound reduces the amount of leukocyte cell infiltration into the eye aqueous humor. In some embodiments, administration of the compound reduces the amount of protein leakage into the eye aqueous humor. In some embodiments, administration of the compound promotes wound healing. In some embodiments, administration of the compound promotes corneal wound healing. In some embodiments, the compound is administered to the skin of a mammal.

In another preferred embodiment, there is provided a method of promoting wound healing, comprising administering cicaprost to an eye. In some embodiments, the cicaprost is present at a concentration of about 0.001% to about 1%, preferably about 0.1%. The method of claim 24, wherein the cicaprost promotes corneal wound healing.

In yet another preferred embdoiment, a pharmaceutical composition comprises a compound of Formula C. In some embodiments, the pharmaceutical composition is an ophthalmic composition. In some embodiments, the pharmaceutical composition is a dermatological composition. The pharmaceutical composition may be provided in a vehicle selected from the group consisting of liquids, solutions, ointments, gels, creams, eye drops, powders, suppositories, sponges, foams, pastes, tinctures, bandages, patches, and implants.

Another preferred embodiment comprises a compound represented by Formula A, its enantiomers, diastereoisomers, tautomers, hydrates, solvates or a pharmaceutically acceptable salt thereof,

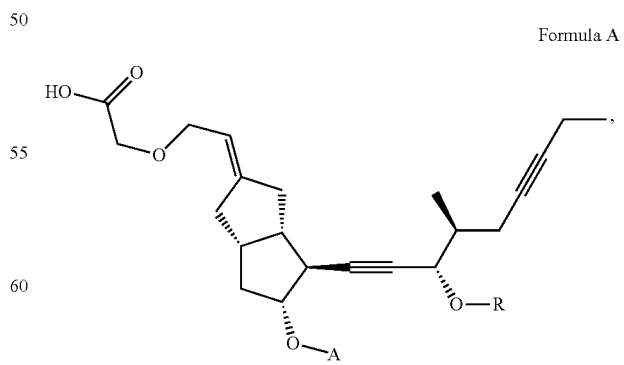

Formula A wherein:
A is selected from the group consisting of hydrogen, acetyl, and —$COCH_2CH_3$; and, R is selected from the group consisting of hydrogen, acetyl, and —COCH$_2$CH$_3$;

wherein A and R are not hydrogen at the same time.

In some embodiments, A is acetyl and R is hydrogen. In some embodiments, A is —COCH$_2$CH$_3$ and R is hydrogen. In some embodiments, A is hydrogen and R is acetyl. In some embodiments, A is hydrogen and R is —COCH$_2$CH$_3$.

In another embodiment, a pharmaceutical composition comprises as an active ingredient a therapeutically effective amount of a compound as defined above (such as Formula A) and a pharmaceutically acceptable carrier.

In some embodiments, the pharmaceutical composition is an ophthalmic composition. In some embodiments, the pharmaceutical composition is a dermatological composition. The pharmaceutical composition may be provided in a vehicle selected from the group consisting of liquids, solutions, ointments, gels, creams, eye drops, powders, suppositories, sponges, foams, pastes, tinctures, bandages, patches, and implants.

In a further embodiment, a method of activating an IP receptor in a mammalian cell comprises administering a compound as defined above (such as Formula A).

Preferably, the compound is an IP receptor agonist. In some embodiments, the compound is administered to a mammal in an amount sufficient to provide a beneficial therapeutic result, wherein the beneficial therapeutic result is selected from the group consisting of reducing inflammation, promoting wound healing, and reducing scarring. In some embodiments, the compound is administered to a mammal in an amount sufficient to at least partially inhibit the production or secretion of inflammatory cytokines and chemokines. In some embodiments, the compound is administered to a mammal in an amount sufficient to at least partially inhibit or reduce the production of at least one selected from the group consisting of IL-8, MCP-1, MIP-1α, MIP-1β, RANTES, and TNF-α. In some embodiments, the compound is administered to a mammal in an amount sufficient to stimulate the production or secretion of VEGF. The compound may be administered to the eye of a mammal. In some embodiments, administration of the compound reduces the amount of leukocyte cell infiltration into the aqueous humor. In some embodiments, administration of the compound reduces the amount of protein leakage into the aqueous humor. In some embodiments, the compound is administered to the skin of a mammal.

DETAILED DESCRIPTION OF INVENTION

Figure 1:
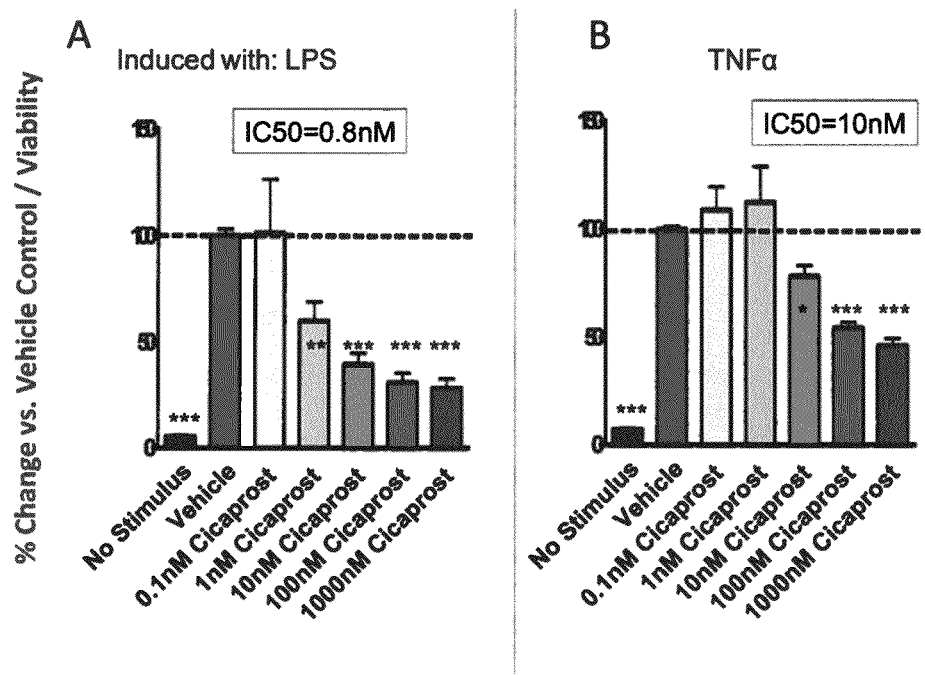
FIGS. 1A-B illustrate the effect of cicaprost on IL-8 secretion in human macrophages subsequent to stimulation with either lipopolysaccharide or TNF-α.

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

The term "alkyl", as used herein, refers to saturated, monovalent or divalent hydrocarbon moieties having linear or branched moieties or combinations thereof and containing 1 to 8 carbon atoms. One methylene (—CH$_2$—) group, of the alkyl group can be replaced by oxygen, sulfur, sulfoxide, nitrogen, carbonyl, carboxyl, sulfonyl, sulfate, sulfonate, amide, sulfonamide, by a divalent C$_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, —$OC_{1-8}$ alkyl groups, —$SC_{1-8}$ alkyl groups, —$C_{1-8}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. One methylene (—$CH_2$—) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon radical having 2 to 6 carbon atoms, derived from a saturated alkyl, having at least one triple bond. One methylene (—$CH_2$—) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —$OC_{1-6}$ alkyl groups, —$SC_{1-6}$ alkyl groups, —$C_{1-8}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl $C_{1-6}$ alkyl groups, sulfoxide $C_{1-6}$ alkyl groups, sulfonamide groups, carbocyclic acid groups, $C_{1-6}$ alkyl carboxylates (ester) groups, amide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehydes, alkylamino groups, amino groups, aryl groups, $C_{3-8}$ cycloalkyl groups or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —$(CO)R_x$ wherein $R_x$ can be alkyl, aryl, cycloalkyl, cycloalkenyl, heterocycle as defined above.

The term "amine" as used herein, represents a group of formula "—$NR_xR_y$", wherein $R_x$ and $R_y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—$SO_2$—".

The term "sulfate" as used herein, represents a group of formula "—O—$S(O)_2$—O—".

The term "sulfonate" as used herein, represents a group of the formula "—$S(O)_2$—O—".

The term "carboxylic acid" as used herein, represents a group of formula "—C(O)OH".

The term "nitro" as used herein, represents a group of formula "—$NO_2$".

The term "cyano" as used herein, represents a group of formula "—CN".

The term "amide" as used herein, represents a group of formula "—$C(O)NR_xR_y$," wherein $R_x$ and $R_y$ can be the same or independently H, alkyl, aryl, cycloalkyl, cycloalkenyl, heterocycle as defined above.

The term "sulfonamide" as used herein, represents a group of formula "—$S(O)_2NR_xR_y$," wherein $R_x$ and $R_y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—$P(O)(OH)_2$".

The term "phosphoric acid" as used herein, represents a group of formula "—$OP(O)(OH)_2$".

The term "sulphonic acid" as used herein, represents a group of formula "—$S(O)_2OH$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Embodiments described herein relate to prostanoid receptor agonists, and in particular those targeting prostanoid IP receptors. Certain compounds, formulations, uses, and other embodiments relate to cicaprost, the structure of which is reproduced below as Formula I,

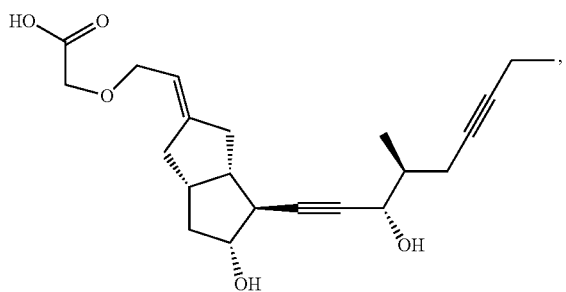

(Formula I)

and include all pharmaceutically acceptable salts, geometrical isomers, enantiomers, diastereoisomers, tautomers, and zwitterions thereof. In some embodiments, cicaprost may be present at a concentration of about 0.001% to about 1%, preferably about 0.1%.

Also disclosed herein are prostanoid IP receptor agonists that are prodrugs of cicaprost. Certain prodrug embodiments include the compound illustrated below as Formula II,

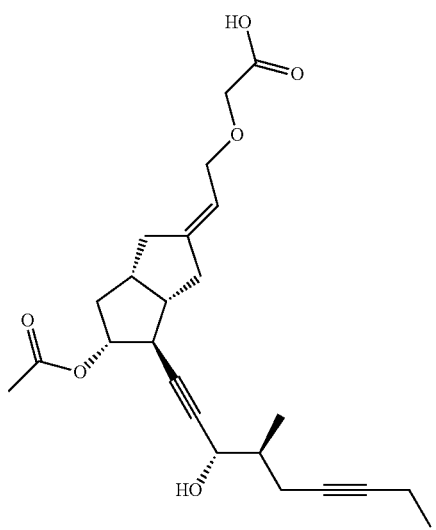

(Formula II)

and include all pharmaceutically acceptable salts, geometrical isomers, enantiomers, diastereoisomers, tautomers, and zwitterions thereof.

Certain prodrug embodiments include the compound illustrated below as Formula III,

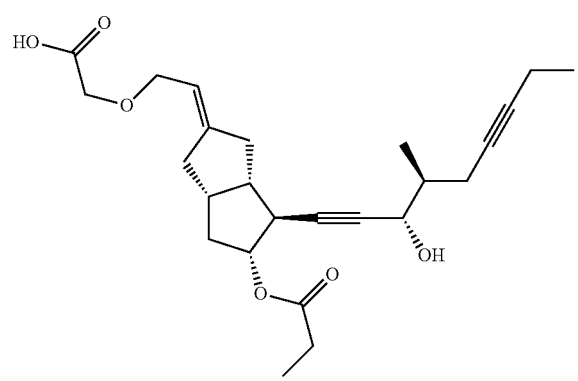

(Formula III)

and include all pharmaceutically acceptable salts, geometrical isomers, enantiomers, diastereoisomers, tautomers, and zwitterions thereof.

Certain prodrug embodiments include the compound illustrated below as Formula IV,

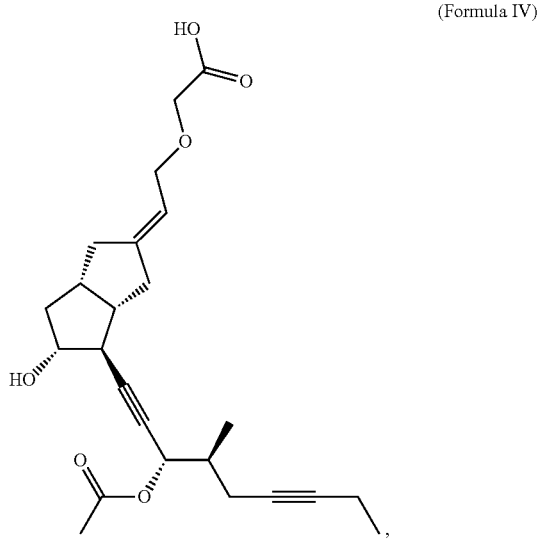 [SMILES: CCC#CC[C@H](C)[C@@H](C#C[C@@H]1[C@H]2C/C(=C/COCC(=O)O)C[C@H]2C[C@H]1O)OC(C)=O]

(Formula IV)

and include all pharmaceutically acceptable salts, geometrical isomers, enantiomers, diastereoisomers, tautomers, and zwitterions thereof.

Certain prodrug embodiments include the compound illustrated below as Formula V,

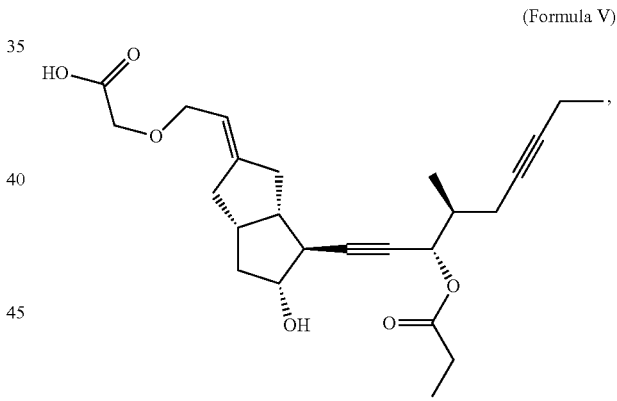

(Formula V)

and include all pharmaceutically acceptable salts, geometrical isomers, enantiomers, diastereoisomers, tautomers, and zwitterions thereof.

A further compound that may be used in conjunction with the embodiments disclosed herein is an IP receptor antagonist compound. In some embodiments, a compound that may be used as such is illustrated below as Formula VI,

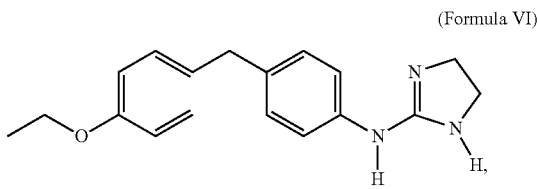

(Formula VI)

Including all pharmaceutically acceptable salts, geometrical isomers, enantiomers, diastereoisomers, tautomers, and zwitterions thereof.

The present disclosure also describes processes for preparing the compounds of Formulas I-V. These compounds can be prepared analogously to conventional methods as understood by the person skilled in the art of synthetic organic chemistry. Synthetic Schemes 1-7 set forth below, illustrate examples of how the compounds according to the invention may be made. It will be of course understood that the synthetic schemes set forth below are only intended for illustrative purposes and are not intended to be limiting, and that the compounds described herein may be synthesized differently.

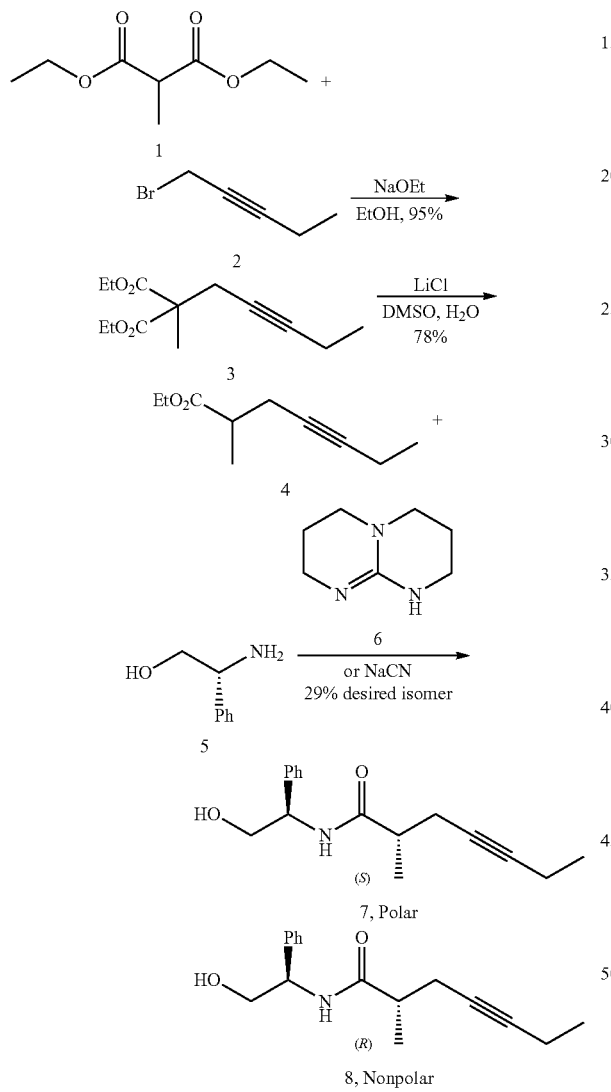

Cicaprost and various other prodrugs thereof were synthesized starting with the scheme described here. Of course, other synthesis schemes are possible and contemplated, and it will be understood that the synthetic scheme described in the foregoing is not intended to be limiting.

Intermediate 3 was prepared by dissolving sodium in ethanol and then adding Intermediate 1 and stirring for 30 minutes, whereupon Intermediate 2 was slowly added to the solution. The resulting slurry was stirred overnight at room temperature, and partially concentrated. Intermediate 3 was extracted with MTBE after the addition of water, and was dried over MgSO₄, filtered, and concentrated to a pale yellow oil. Treatment of Intermediate 3 with lithium chloride in an oil bath heated to 189° C. continued until gas evolution stopped. The mixture was cooled, poured into water, and extracted with MTBE. Drying over MgSO₄ was performed and the Intermediate 4 was concentrated into an orange oil.

Intermediate 4 had the ester converted to its acid, followed by preparation of an amide by activation of the acid. Sodium cyanide was used as a catalyst to trans-esterify the Intermediate 4 ester with the Intermediate 5 alcohol, which then underwent an amide formation to give a mixture of Intermediates 7 and 8 after heating to 110° C. overnight. The mixture was taken up in ethyl acetate and washed with water, followed by concentration. Of these Intermediates 7 and 8, the more polar isomer may be separated by chromatography. The Catalyst 6 was also tested in the reaction and surprisingly found to be much faster, yielding complete conversion to the mixture of amides within 2-3 h as opposed to days using sodium cyanide.

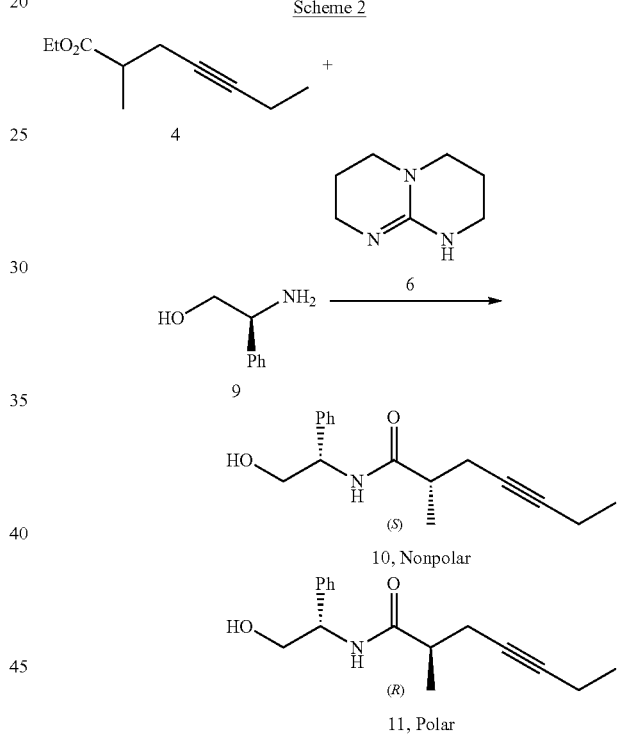

Scheme 2 illustrates an alternative synthetic route for arriving at the Intermediates 7 and 8 above, and which correspond to Intermediates 10 and 11 in this Scheme. Intermediates 4 and 9 were combined and heated to 100° C. overnight, and otherwise prepared as described in the previous scheme. Here, using the opposite enantiomer of the Intermediate 5, Intermediate 9, was used so that the desired isomer would elute first from the chromatography column and thus be much more easily isolated.

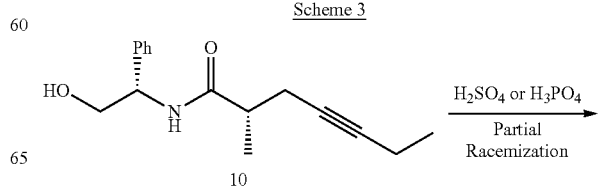

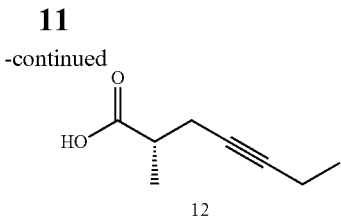

Scheme 3 illustrates the hydrolysis of Intermediate 10 (although Intermediate 7 may also be used here) with sulfuric or phosphoric acid in dioxane. Some racemization of the amides was found to occur during hydrolysis, however.

Additionally, the Intermediate 8 and 11 isomers (Schemes 1 and 2) may also be easily be hydrolyzed back to the acid with hot 50% NaOH/propanol. The acid was esterified with dimethylsulfate/DMF/$K_2CO_3$ to give Intermediate 4 which could then be recycled back into the resolution process.

Treatment of Intermediate 13 with phosphonate anions yielded Intermediate 15. Here, phosphonic acid, methyl-, dimethyl ester was dissolved in THF and cooled to −78° C., upon which n-butyllithium in hexane was added to the mixture and stirred for 30 minutes. Intermediate 13 dissolved in THF was then added. The mixture was stirred for 1 hour, warmed to 0° C., and quenched with 10% citric acid solution. The mixture was then isolated with ethyl acetate, washed with brine, and concentrated, followed by Kugelrohr distillation to obtain the Intermediate 15 as a clear oil.

Purification via chromatography was used to remove some of the reaction product that reacted with the wrong carbonyl group. Intermediate 15 was found to have positive rotation, which confirmed the stereochemistry of this side chain.

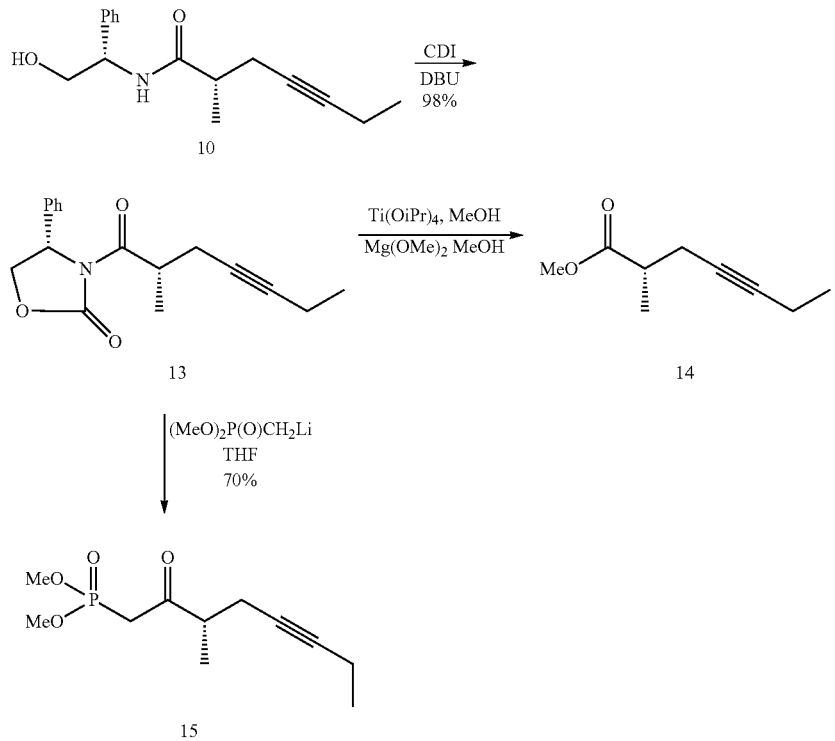

As an alternative to Scheme 3 above, the Intermediate 10 was converted to the Intermediate 13. Carbonyldiimidazole (CDI) was used to treat Intermediate 10, being dissolved in THF, in the presence of one equivalent of 1,8-diazabicycloundec-7-ene (DBU). The mixture was stirred overnight at room temperature. The mixture was then cooled to 0° C. and 1,8-diazabicyclo[5.4.0]undec-7-ene was added and stirred for 2 hours. The resulting mixture was added into water and extracted with ethyl acetate, and dried and concentrated. Titanium isopropoxide or magnesium methoxide, in methanol, were used to create the Intermediate 14 ester.

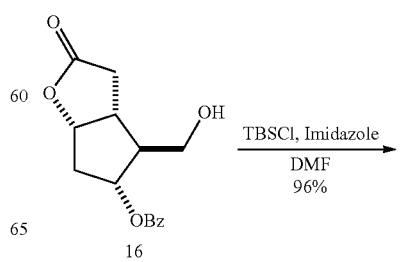

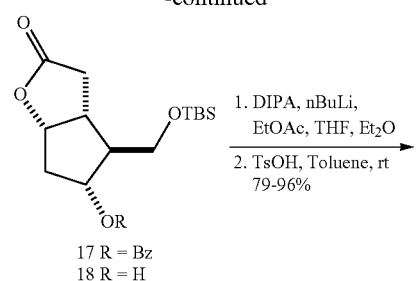
17 R = Bz
18 R = H
1. DIPA, nBuLi, EtOAc, THF, Et$_2$O
2. TsOH, Toluene, rt
79-96%
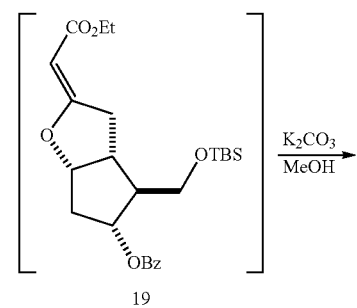
19
K$_2$CO$_3$ / MeOH
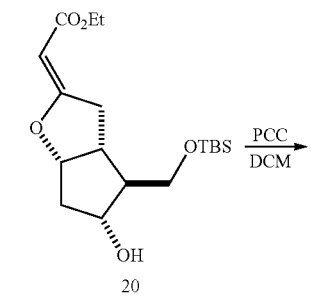
20
PCC / DCM
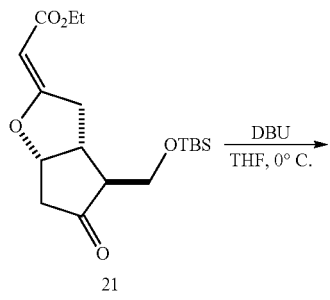
21
DBU / THF, 0° C.
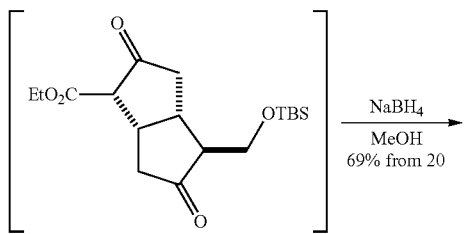
22
NaBH$_4$ / MeOH
69% from 20
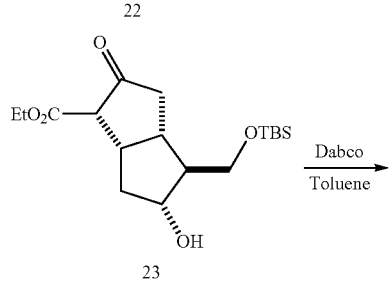
23
Dabco / Toluene
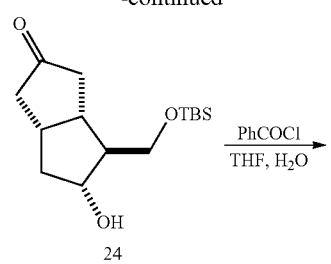
24
PhCOCl / THF, H$_2$O
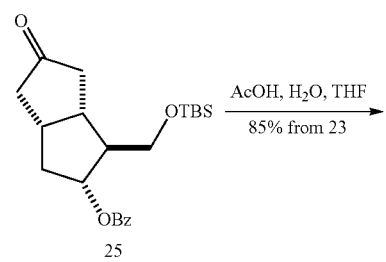
25
AcOH, H$_2$O, THF
85% from 23
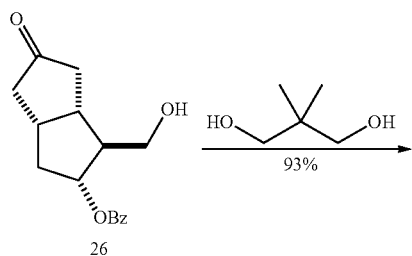
26
HO—⟨⟩—OH
93%
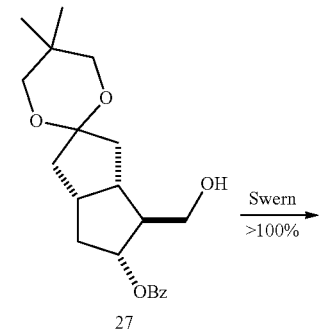
27
Swern
>100%
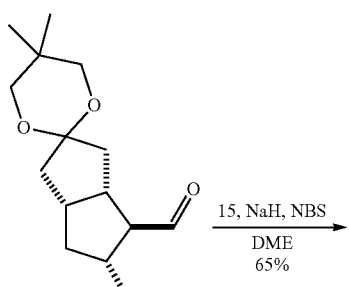
28
15, NaH, NBS
DME
65%

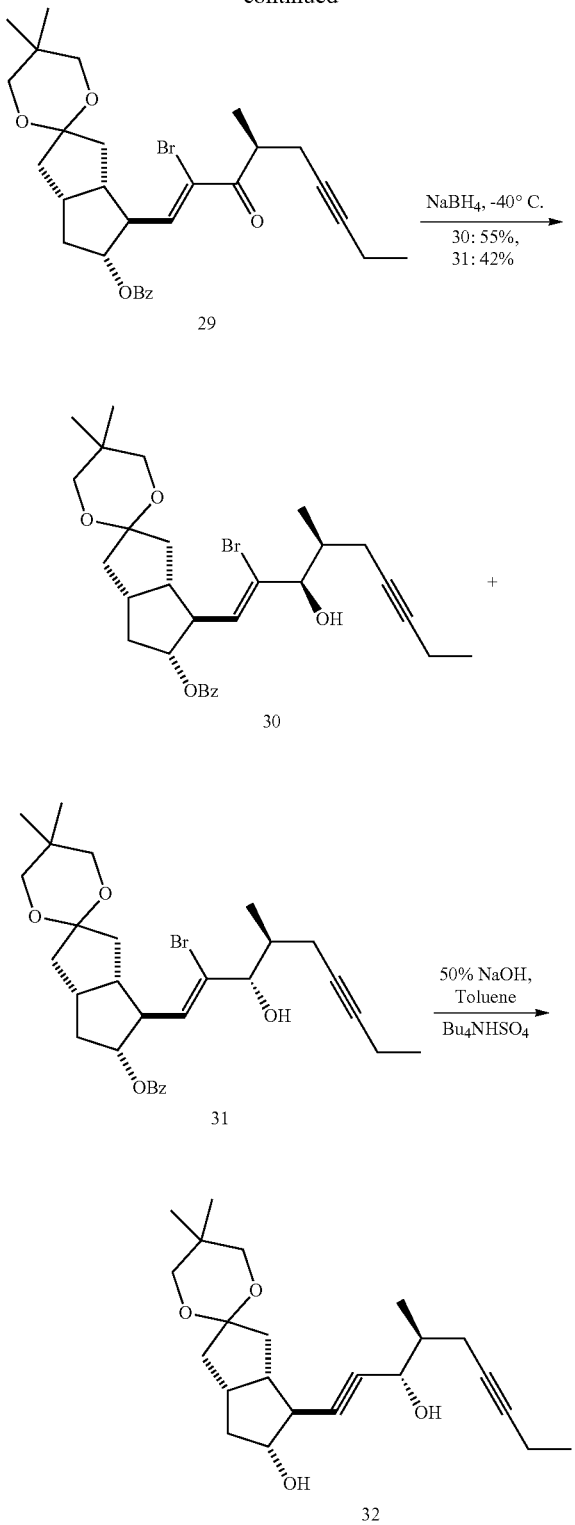

In Scheme 5, the other portion of cicaprost was synthesized as illustrated above to form Intermediate 28, which was then joined with Intermediate 15 from Scheme 4 to eventually produce cicaprost.

Intermediate 16 was dissolved in DMF, and treated at 0° C. with 1H-imidazole and TBSCl. After stirring overnight at room temperature, the product was poured into water and extracted with MTBE, followed by crystallization in cold hexane and vacuum drying at 50° C. for 2 days.

N,N-diisopropylamine was dissolved in heptane and cooled to −78° C. n-butyllithium in hexane was then added, while keeping the temperature below −35° C. When the addition was complete the mixture was stirred for 15 min and then ethyl acetate was slowly added keeping the temperature below −70 C. After stirring for 15 min, a solution of Intermediate 17 in ether and tetrahydrofuran was slowly added. After 1 hour, the solution was poured into a citric acid solution and the product extracted with MTBE. The crude was taken up in toluene and treated with p-toluenesulfonic acid with $MgSO_4$ to yield Intermediate 19. The mixture was filtered and washed with bicarbonate and concentrated to yield an oil. The oil was taken up in methanol and treated with potassium carbonate. The mixture was poured into MTBE and then water added. The mixture was then extracted with MTBE and chromatographed on silica to give a clear oil which was Intermediate 20.

A jacket flask with mechanical stirrer cooled to 17° C. was charged with methylene chloride, aluminum oxide, and pyridinium chlorochromate. Intermediate 20 in 100 mL of DCM was then added to the slurry of oxidant and the temperature raised to 23° C. Ether was added to the mixture and then filtered through a plug of magnesol using MTBE to rinse the cake. The solution was concentrated to an oil (Intermediate 21) and transferred to a jacketed flask with tetrahydrofuran, and cooled to 0° C. DBU was then added and the solution stirred for 1.5 h to yield Intermediate 22. The mixture was cooled to −20° C. and sodium tetrahydroborate slowly added. The mixture was stirred at −20° C. for 2.5 h and then quenched with acetone. After the acetone was added, stirring was continued for 10 minutes and the entire mixture was then transferred to a solution of citric acid with ice. The solution was extracted three times with MTBE, washed with water, bicarbonate, and brine. The organic solution was stored at −20° C. overnight, and then dried over $MgSO_4$, followed filtered through a pad of Magnesol yielding an oil as Intermediate 23.

Intermediate 23 in toluene was treated with triethylenediamine and water, and heated to 110° C. for 5 h. The mixture was cooled and concentrated to give a thick slurry, which comprised Intermediate 24. The slurry was treated with 1 L of THF and cooled in an ice bath. Benzoyl chloride was then added, while keeping the temperature below 6° C., to yield Intermediate 25. The mixture was treated with water and warmed to room temperature. Intermediate 25 was isolated with MTBE after addition to water. After washing with water and brine, concentration affords a brown oil. The oil was taken up in acetic acid, water, THF, and phosphoric acid at room temperature, and stirred until the TBS deprotection was nearly complete. The resulting Intermediate 26 was extracted with ethyl acetate, washed with bicarbonate and concentrated, followed by silica chromatography.

Intermediate 26 was dissolved in benzene and treated with neopentyl glycol and pyridinium p-toluenesulfonate, followed by reflux heating with Dean-Stark water removal. The mixture was cooled and washed with saturated bicarbonate, brine, and then concentrated. The solid product was crystallized from MTBE hexane to yield Intermediate 27.

Intermediate 27 was dissolved in methylene chloride, was cooled to −78° C., and treated with a solution of DMSO in an equal volume of DCM. This mixture was stirred for 1.5 hours and then treated slowly with triethylamine and allowed to stir at −78° C. for 1 hour and then warmed to 0° C. At this point the mixture was poured into water and the product extracted with DCM. The organic was dried over MgSO₄ and concentrated after filtration to give a viscous oil which was Intermediate 28.

Intermediate 15 was brominated, and then reacted together with Intermediate 28. Specifically, Intermediate 15 was dissolved in 1,2-dimethoxyethane, cooled in an ice bath, and treated with 60% NaH dispersion (60:40, sodium hydride: mineral Oil). The mixture was stirred for 30 minutes, followed by addition of N-bromosuccinimide and further stirring for about 3 hours. Intermediate 28 was added to the previous mixture and stirred with warming overnight. The next day, the crude mixture was poured into water and extracted with MTBE to give a clear oil which was chromatographed to yield Intermediate 29.

Intermediate 29 was dissolved in methanol and cooled to −45° C. in a dry ice ACN bath. Sodium tetrahydroborate was then added and the mixture stirred for 2 hours. The reaction was quenched with acetone and then partially concentrated before pouring into water and extracting with MTBE three times. The mixture was then washed with water and brine. Intermediate 29 was purified using chromatography and reduced at −40° C. to yield a 1:1 mixture of Intermediates 30 and 31. Intermediate 30 was slightly more prevalent, but was separated out via chromatography.

Intermediate 31 was dissolved in toluene and treated with sodium hydroxide dissolved in water, followed by addition of N,N,N-tributylbutan-1-aminium hydrogen sulfate at room temperature. The mixture was stirred for 3 hours, and then poured into water, with the product extracted with ethyl acetate. The crude mixture was taken up in methanol and treated at room temperature with potassium carbonate for 2 hours to yield Intermediate 32.

Scheme 6

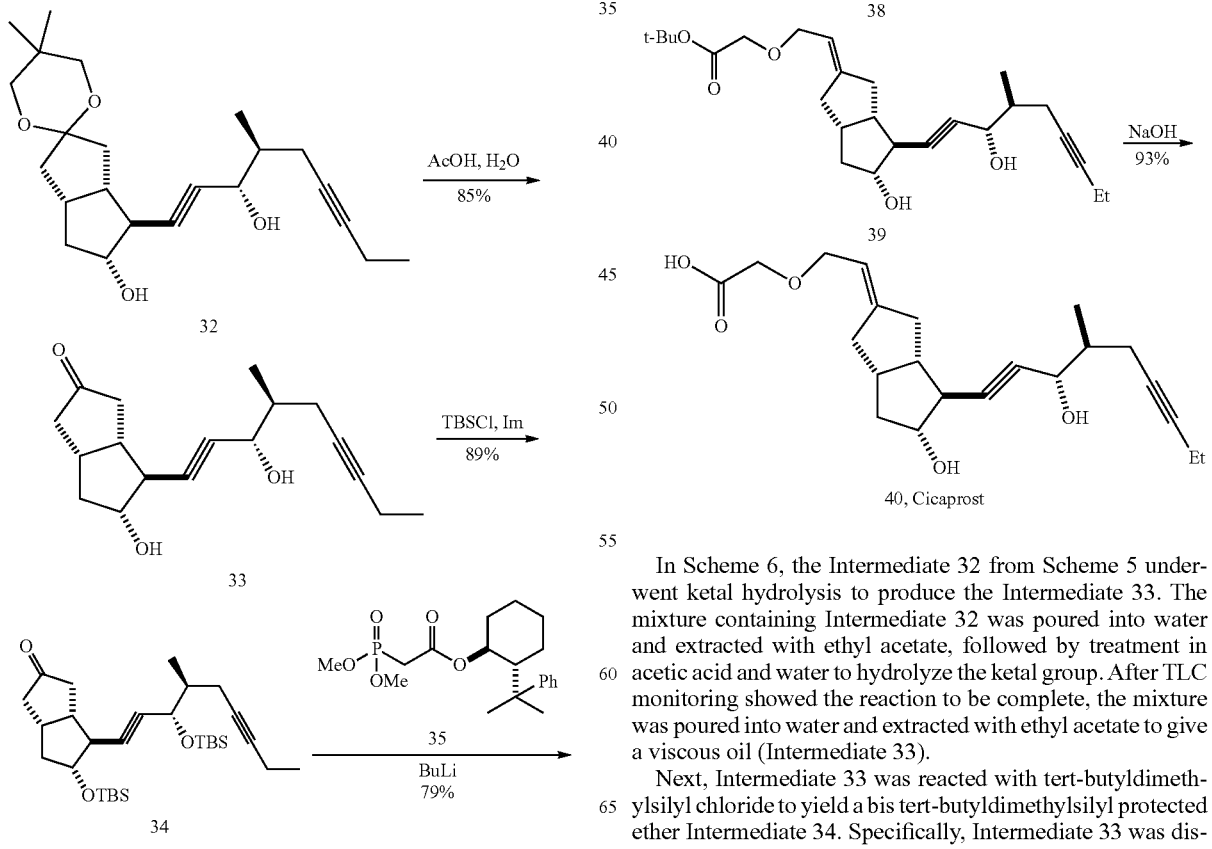

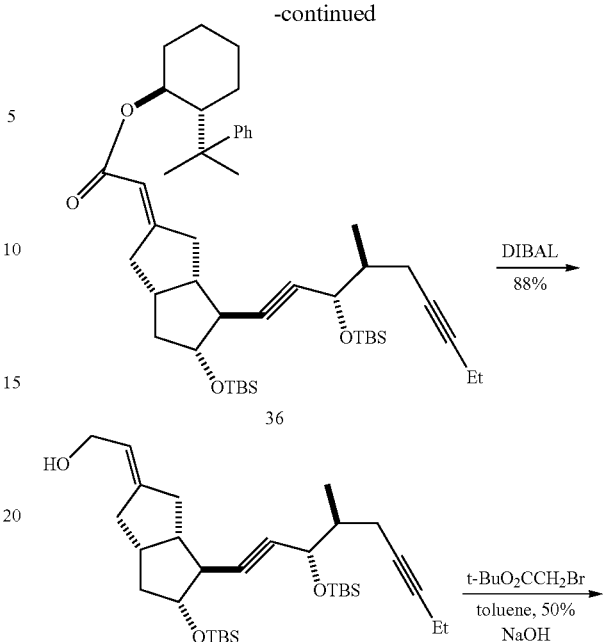

In Scheme 6, the Intermediate 32 from Scheme 5 underwent ketal hydrolysis to produce the Intermediate 33. The mixture containing Intermediate 32 was poured into water and extracted with ethyl acetate, followed by treatment in acetic acid and water to hydrolyze the ketal group. After TLC monitoring showed the reaction to be complete, the mixture was poured into water and extracted with ethyl acetate to give a viscous oil (Intermediate 33).

Next, Intermediate 33 was reacted with tert-butyldimethylsilyl chloride to yield a bis tert-butyldimethylsilyl protected ether Intermediate 34. Specifically, Intermediate 33 was dissolved in DMF and treated with 1H-imidazole and tert-butyldimethylsilyl chloride, and stirred at room temperature for 3 hours. The mixture was poured into water and extracted with MTBE to give a clear oil, followed by chromatography on silica with 0-30% ethyl acetate to yield Intermediate 34.

Intermediate 34 was then olefinated using the chiral phosphonate Intermediate 35 in a six-day reaction to yield Intermediate 36. First, Intermediate 35 was dissolved in tetrahydrofuran and cooled to −80° C. N-butyllithium in hexane was then added, while keeping the temperature below −60° C. The solution was cooled to −80° C. and then treated with a solution of Intermediate 34 dissolved in THF. The mixture was stirred at −66° C. for 6 days then warmed to −30° C. for 24 hours. The bath was then removed and the solution warmed to 0° C. before quenching with 10% citric acid solution. The product was extracted with ethyl acetate and concentrated to an oil, followed by silica gel chromatography to yield Intermediate 36.

Ester reduction on Intermediate 36 was then performed, and the resulting Intermediate 37 underwent etherification to yield Intermediate 38. Here, Intermediate 36 was dissolved in THF and cooled in an ice bath. Diisobutylaluminum hydride in toluene was added and the mixture stirred at room temperature for 2 hours. The mixture was quenched with phosphoric acid and water, yielding a gel. Citric acid was added along with more water, and the product was extracted with MTBE, and chromatographed on silica to yield Intermediate 37. Intermediate 37 was next dissolved in toluene and treated with aqueous sodium hydroxide and tetrabutylammonium hydrogen sulfate. The mixture was stirred at room temperature overnight. Water was added to separate the layers, which were further washed with water, concentrated, and chromatographed on silica to yield Intermediate 38.

Next, Intermediate 38 was dissolved in THF and treated with tetrabutylammonium fluoride trihydrate in THF at room temperature overnight. The mixture was poured into water and extracted with ethyl acetate, washed with brine, and dried over $MgSO_4$. Subsequently, the mixture was filtered, concentrated, and chromatographed on silica gel with ethyl acetate-hexane, yielding Intermediate 39. Intermediate 39 was dissolved in methanol and treated with sodium hydroxide, the mixture then being stirred at room temperature overnight. The mixture was then quenched into a pH 3 phosphate buffer and the product extracted with ethyl acetate, followed by a wash with water and brine. The product was then dried over $MgSO_4$, filtered, and concentrated to a viscous oil. This yielded cicaprost (Formula I, or Intermediate 40 as illustrated above).

Formula I was found to be a clear, viscous oil,

Scheme 7

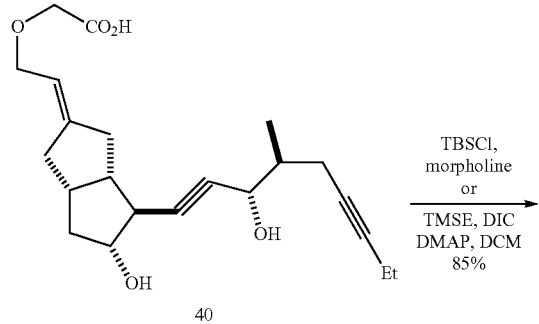

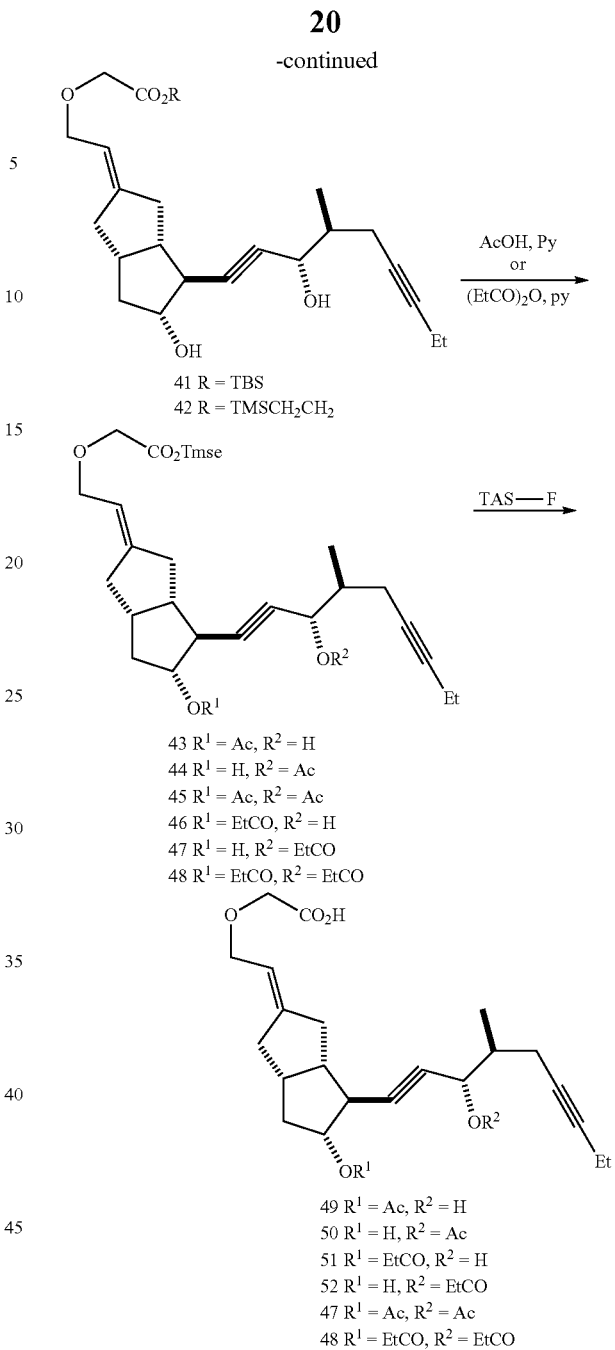

Cicaprost, labeled as Intermediate 40 above, may then be used to create various prodrugs, including those illustrated above in Formulas II-V. In this scheme 7, the carboxyl group on cicaprost was protected with TBS to yield Intermediate 41, or trimethylsilylethyl ester to yield Intermediate 42. It may be preferable to make Intermediate 42 instead of Intermediate 41, as there may be some slight silylation of the alcohol groups when TBS is used. The trimethylsilylethyl ester may be preferable as this is cleavable in the presence of an acetate when tris(dimethylamino)sulfonium difluorotrimethylsilicate (TAS-F) is used for deprotection. As such, Intermediate 40 was dissolved in methylene chloride and treated with 2-(trimethylsilyl)ethanol, 4-dimethylaminopyridine, and N,N'-dicyclohexylcarbodiimide while stirring at room temperature. After 30 minutes, a precipitate formed and TLC (50% acetone hexane) showed formation of a new product.

After further stirring for two hours, the product was isolated with ethyl acetate and chromatographed on silica to yield a clear oil as Intermediate 42.

Intermediate 42 was prepared using dicyclohexylcarbodiimide (DCC) or diisopropylcarbodiimide (DIC) in the presence of an excess of the Intermediate 40 and dimethylaminopyridine (DMAP). An excess is preferably used to ensure that no polymer type products are formed.

Intermediates 46, 47, and 48 were prepared from Intermediate 42. Here, Intermediate 42 was taken up in pyridine at room temperature and treated with propanoic acid anhydride in toluene, and allowed to stand at room temperature. TLC after 30 minutes showed three new products forming. After 5 hours, the mixture was poured into water and extracted with ethyl acetate, dried over $MgSO_4$ and concentrated to an oil. The oil was chromatographed on silica with 0-50% ethyl acetate-hexane to yield Intermediates 46, 47, and 48. Chromatography resulted in the Intermediate 48 coming out first, followed by Intermediate 46, and last, Intermediate 47.

Deprotection of Intermediates 46, 47 and 48, yielded Compounds 51 and 52 (Formulas III and V, respectively), as well as Compound 48. To accomplish this, either of Intermediates 46, 47, and 48 were dissolved in DMF at room temperature and treated with a solution of tris(dimethylamino)sulfonium difluorotrimethylsilicate in N,N-dimethylformamide prepared in a dry box. The solution was allowed to stand for 2 hours at which point monitoring with TLC showed a complete reaction. The mixture was poured into ethyl acetate, acidified with citric acid, extracted with ethyl acetate, twice washed with water, and then dried over $MgSO_4$. Concentration afforded a viscous clear oil. The crude was chromatographed on silica to yield the respective Compounds 51, 52, and 54.

Intermediate 42 may similarly be treated with one equivalent of acetic anhydride (instead of propanoic acid anhydride) in pyridine to give a mixture of 3 products (Intermediates 43, 44, and 45). Chromatography was used to separate the respective Intermediates 43, 44, and 45, which may also be distinguished via NMR. Similarly to what has been explained above, Intermediates 43, 44, and 45 may be deprotected to yield Compounds 49 and 50 (Formulas II and IV, respectively), together with Compound 45. These were purified using silica gel chromatography. Formulas II-V were also hydrolyzed back to cicaprost and chromatographed via HPLC to confirm purity.

It has recently been discovered that cicaprost and its other prodrugs discussed above (e.g., Formulas I-V) act as agonists to the prostacyclin ("IP") receptor. The IP receptor is a G-protein coupled receptor that is found in various body cells, including macrophages. Cicaprost and its other prodrugs (for example, Formulas II-V), may serve to trigger a response by IP receptors found in cells by virtue of their activity as IP receptor agonists. Specifically, it is believed that cicaprost and its other prodrugs stimulate IP receptors found in mammalian cells so as to inhibit inflammation and stimulate factors important for wound healing. Advantageously, and as discussed in greater detail below, it has been found that cicaprost and other related prodrugs possess IP receptor agonist activity, often at very low concentrations.

The use of the compounds disclosed herein as IP receptor agonists may be advantageous in providing beneficial therapeutic results to a patient or animal. For example, use of IP receptor agonists such as those disclosed herein may aid in reducing inflammation, promoting wound healing, and reducing scarring.

Without wishing to be bound by theory, it is believed that deleterious effects as a result of inflammation and inflammatory diseases may be reduced by the use of IP receptor agonists disclosed herein, inasmuch as these may at least partially inhibit or reduce the production or secretion of key inflammatory cytokines and chemokines. In some embodiments, these IP receptor agonists may at least partially inhibit or reduce the production or secretion of interleukins, including IL-8, MCP-1, macrophage inflammatory proteins, including MIP-1α and MIP-1β, RANTES, and tumor necrosis factors, including TNF-α. In some embodiments, IP receptor agonists disclosed herein may also stimulate the production or secretion of certain growth factors and signal proteins, including VEGF.

IP receptor agonists including cicaprost and other related prodrugs disclosed herein may also have other effects. For example, cicaprost has been found to inhibit inflammatory cell infiltration, for example by lymphocytes, macrophages, and other inflammatory cells, in regions such as blood vessels and lymph nodes surrounding an inflamed site. These compounds may also inhibit aqueous protein leakage.

Preferably, the use of the IP receptor agonist compounds disclosed herein may be beneficial in treating inflammation relating to infections or autoimmune diseases. In some embodiments, the IP receptor agonist compounds disclosed herein may be applied topically. Topical treatment as defined herein includes dermal, ocular, nasal, buccal, rectal, and other administration to skin or mucous membranes. Suitable vehicles for administration include all known formulations and methods, including liquids, solutions, ointments, gels, creams, eye drops, powders, suppositories, sponges, foams, pastes, tinctures, and so forth.

Administration may also be performed via other vehicles, including implants or other formulations that permit implantation and short-to-long term delivery of the respective IP agonist compound within or in proximity to a tissue site, wound site, or body organ. For example, the compound or compounds may be formed into an implant for placement within a wound site. The compound or compounds may also be formed as an implant for placement over a mucous or dermal surface, including as an ocular implant. Bandages and patches, including transdermal patches, are also envisioned. Less preferably, the IP agonist compounds disclosed herein may be administered systemically (i.e., via injection or solid dosage), as well as any other suitable administration route.

IP receptor agonist compounds, including those disclosed herein, may be useful for the treatment of various diseases and conditions, including inflammation, wound healing, and scar reduction. Systemically, these compounds may be beneficial in the treatment of autoimmune diseases, including rheumatoid arthritis. Reduction of blood pressure may also be possible. Allergies may also be alleviated by use and administration of these compounds. Administration and use of the IP receptor agonist compounds disclosed herein may also be useful for dermal conditions including psoriasis, dermatitis, rosacea, acne, allergic conditions, burns, and dermal wounds (e.g., incisions, cuts, and scrapes). Administration and use of the IP receptor agonist compounds disclosed herein may also be beneficial for the treatment of ocular conditions such as dry eye, conjunctivitis, uveitis, and ocular wounds (including incisions as a result of radial keratotomies or LASIK® procedures).

The following describes various experiments that were conducted to determine the effect of the IP receptor agonist compounds described herein.

Example 1

FIGS. 1A-B illustrate the effect of cicaprost on IL-8 secretion on in vitro human macrophages. The human macrophages were simulated either with lipopolysaccharide (LPS), illustrated in FIG. 1A, or with TNF-α, illustrated in FIG. 1B. The labels on the x-axis correspond respectively to tests measuring IL-8 concentration with no stimulus, a control of only stimulant vehicle (i.e., LPS or TNF-α), and stimulant vehicle in conjunction with cicaprost concentrations of 0.1 nM, 1 nM, 10 nM, 100 nM, and 1000 nM. The y-axis tracks the percentage change of concentration of IL-8 versus the control stimulant vehicle, which is set at 100%.

In FIG. 1A, the half-maximal inhibitory concentration ($IC_{50}$) of cicaprost on IL-8 secretion stimulated by LPS corresponded to 0.8 nM. In FIG. 1B, the $IC_{50}$ of cicaprost on MCP-1 secretion corresponded to 10 nM.

Example 2

Figure 2:
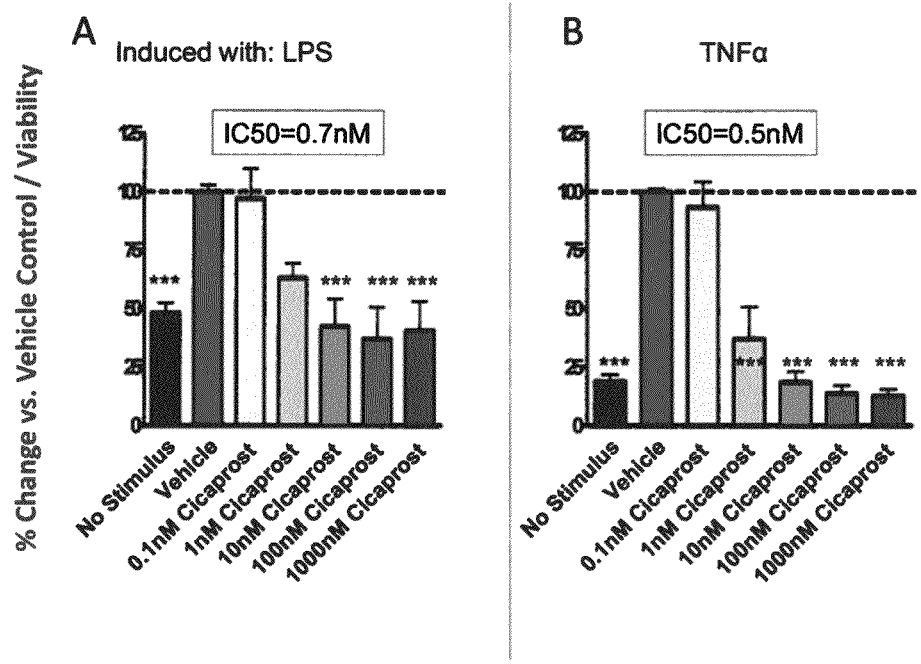
FIGS. 2A-B illustrate the effect of cicaprost on MCP-1 secretion in human macrophages subsequent to stimulation with either lipopolysaccharide or TNF-α.

FIGS. 2A-B illustrate the effect of cicaprost on MCP-1 secretion on in vitro human macrophages. The human macrophages were simulated either with LPS, illustrated in FIG. 2A, or with TNF-α, illustrated in FIG. 2B. The labeling of the graphs is otherwise the same as described above.

In FIG. 2A, the $IC_{50}$ of cicaprost on MCP-1 secretion stimulated by LPS corresponded to 0.7 nM. In FIG. 2B, the $IC_{50}$ of cicaprost on MCP-1 secretion corresponded to 0.5 nM.

Example 3

Figure 3:
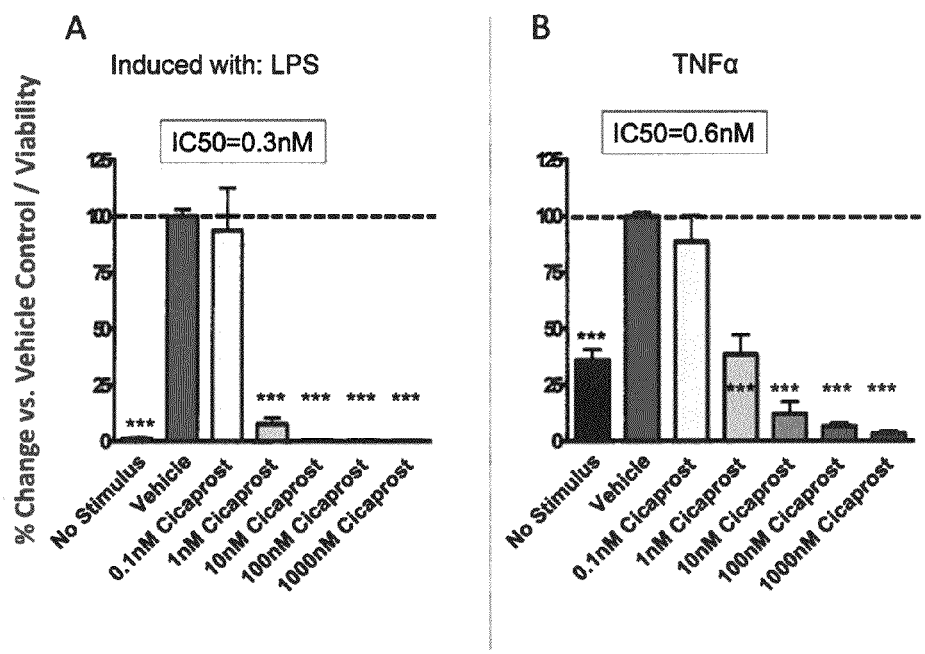
FIGS. 3A-B illustrate the effect of cicaprost on MIP-1α secretion in human macrophages subsequent to stimulation with either lipopolysaccharide or TNF-α.

FIGS. 3A-B illustrate the effect of cicaprost on MIP-1α secretion on in vitro human macrophages. The human macrophages were simulated either with LPS, illustrated in FIG. 3A, or with TNF-α, illustrated in FIG. 3B. The labeling of the graphs is otherwise the same as described above.

In FIG. 3A, the $IC_{50}$ of cicaprost on MIP-1α secretion stimulated by LPS corresponded to 0.3 nM. In FIG. 3B, the $IC_{50}$ of cicaprost on MIP-1α secretion corresponded to 0.6 nM.

Example 4

Figure 4:
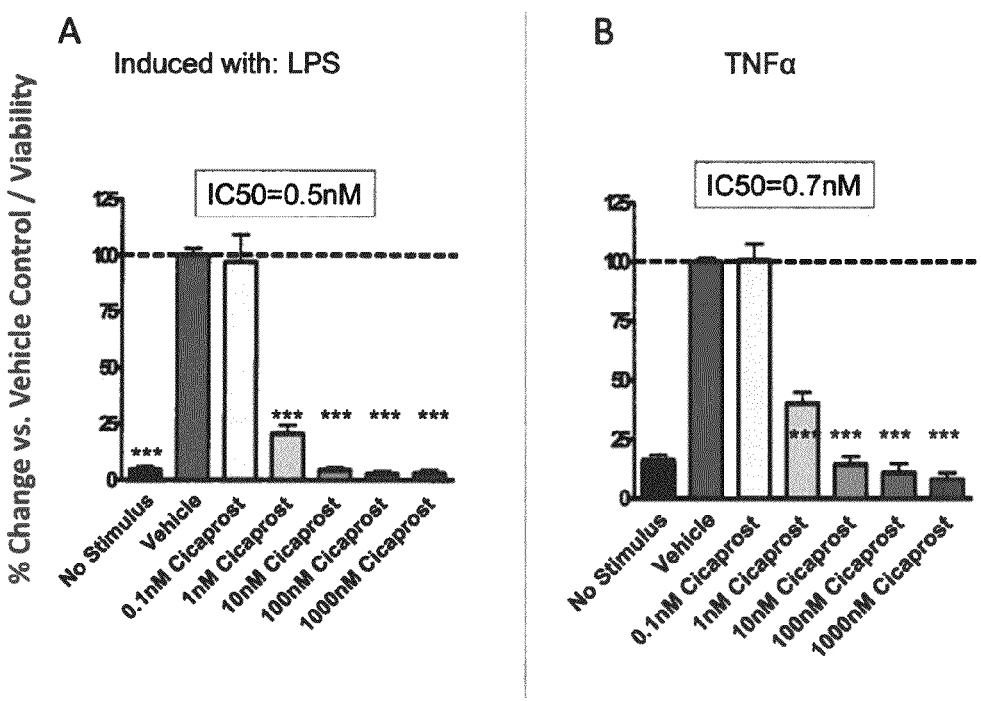
FIGS. 4A-B illustrate the effect of cicaprost on MIP-1β secretion in human macrophages subsequent to stimulation with either lipopolysaccharide or TNF-α.

FIGS. 4A-B illustrate the effect of cicaprost on MIP-1β secretion on in vitro human macrophages. The human macrophages were simulated either with LPS, illustrated in FIG. 4A, or with TNF-α, illustrated in FIG. 4B. The labeling of the graphs is otherwise the same as described above.

In FIG. 4A, the $IC_{50}$ of cicaprost on MIP-1β secretion stimulated by LPS corresponded to 0.5 nM. In FIG. 4B, the $IC_{50}$ of cicaprost on MIP-1β secretion corresponded to 0.7 nM.

Example 5

Figure 5:
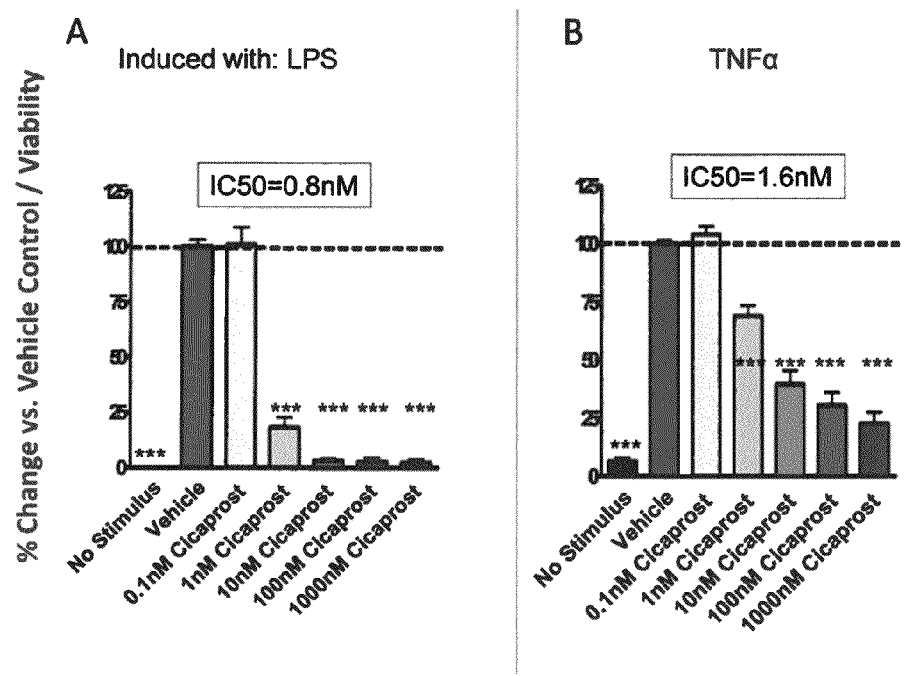
FIGS. 5A-B illustrate the effect of cicaprost on RANTES secretion in human macrophages subsequent to stimulation with either lipopolysaccharide or TNF-α.

FIGS. 5A-B illustrate the effect of cicaprost on RANTES secretion on in vitro human macrophages. The human macrophages were simulated either with LPS, illustrated in FIG. 5A, or with TNF-α, illustrated in FIG. 5B. The labeling of the graphs is otherwise the same as described above.

In FIG. 5A, the $IC_{50}$ of cicaprost on RANTES secretion stimulated by LPS corresponded to 0.8 nM. In FIG. 5B, the $IC_{50}$ of cicaprost on RANTES secretion corresponded to 1.6 nM.

Example 6

Figure 6:
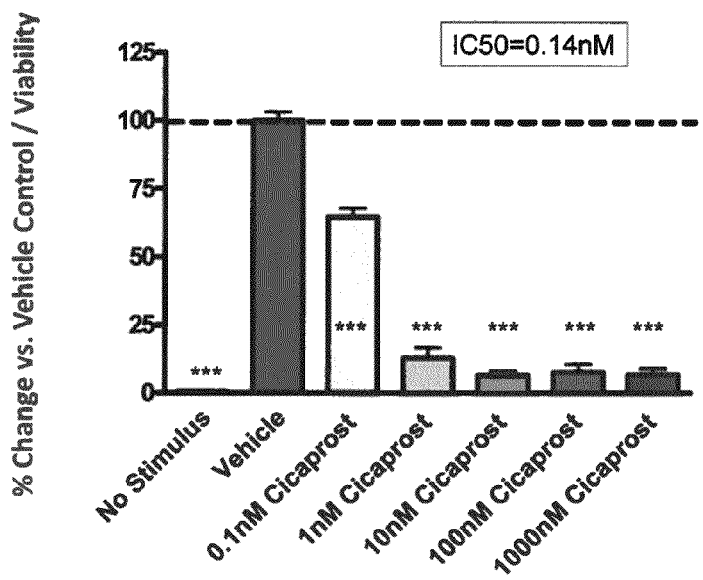
FIG. 6 illustrates the effect of cicaprost on TNF-α secretion in human macrophages subsequent to stimulation with lipopolysaccharide.

FIG. 6 illustrates the effect of cicaprost on TNF-α secretion on in vitro human macrophages. The human macrophages were simulated with LPS. The labeling of the graphs is otherwise the same as described above. Here, the $IC_{50}$ of cicaprost on TNF-α secretion corresponded to 0.14 nM.

Example 7

Figure 7:
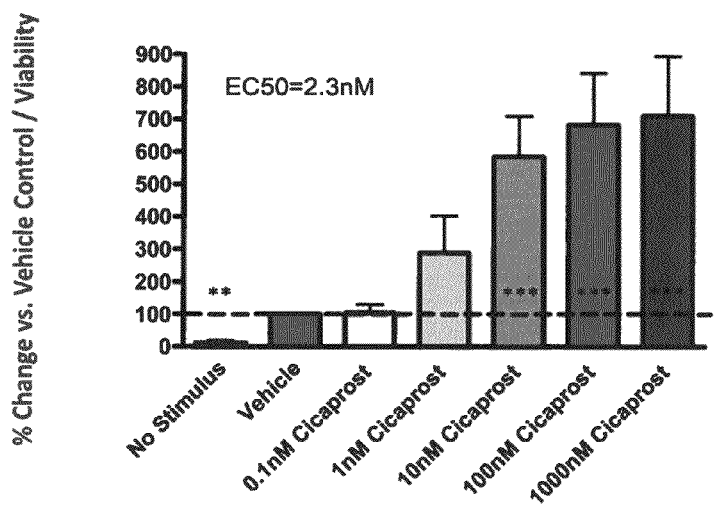
FIG. 7 illustrates the effect of cicaprost on VEGF secretion in human macrophages subsequent to stimulation with TNF-α.
Figure 8:
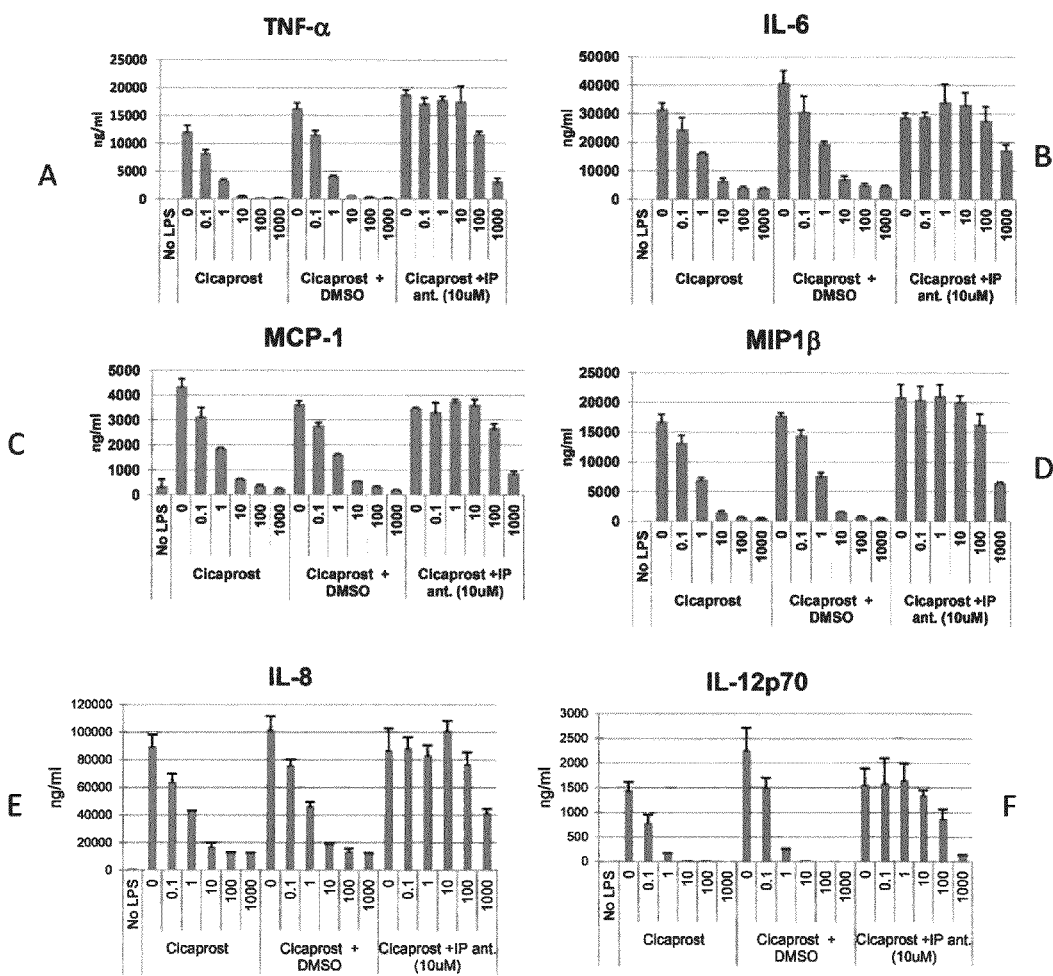
FIGS. 8A-F illustrate the effect of cicaprost, cicaprost with DMSO, and cicaprost with an IP receptor antagonist on cytokine secretion in lipopolysaccharide-stimulated human monocyte derived dendritic cells.

FIG. 7 illustrates the effect of cicaprost on VEGF secretion on in vitro human macrophages. The human macrophages were simulated with TNF-α. The labeling of the graphs is otherwise the same as described above. Surprisingly, cicaprost was found to have an excitatory effect on VEGF secretion subsequent to stimulation with TNF-α, in contrast to the other examples described herein where cicaprost had an inhibitory effect. Here, the half maximal effective concentration ($EC_{50}$) of cicaprost on VEGF secretion corresponded to 2.3 nM.

Example 8

FIGS. 8A-F illustrate the effect of different IP receptor agonists and antagonists on cytokine secretion in human monocyte derived dendritic cells stimulated with LPS. In these experiments, the cells were exposed to cicaprost, cicaprost in conjunction with DMSO, and cicaprost with an IP receptor antagonist (Formula VI). Cytokines measured for were TNF-α, IL-6, MCP-1, MIP-1β, IL-8, and IL-12p70, corresponding to FIGS. 8A through 8F, respectively. The concentration ranges of cicaprost were 0 nM, 0.1 nM, 1 nM, 10 nM, 100 nM, and 1000 nM. The concentration of Formula VI IP receptor antagonist used was 10 uM throughout. The concentration of the various cytokines tested for were measured in ng/ml. The concentration of the DMSO used in conjunction with cicaprost was at 0.1%.

As the concentration of cicaprost and cicaprost with DMSO increased, both were found to exhibit increasing inhibition of cytokine expression, as evidenced by the reduced concentrations of the respective cytokines with respect to the control with 0 nM cicaprost/cicaprost with DMSO. Addition of the IP receptor antagonist Formula VI caused cytokine expression to remain elevated in comparison, and, at lower cicaprost concentration ranges, closer to the control level of cytokine release. As such, because a clear relation was found between inhibition of cytokine production due to IP receptor agonists, and cessation of the inhibition subsequent to the addition of an IP receptor antagonist, it can be demonstrated that cicaprost specifically targets cytokine production via the IP receptor.

Example 9

FIGS. 9A-D show the results of experiments where cicaprost was applied topically to inhibit inflammation in a rat endotoxin-induced uveitis (EIU) model. Here, the rats were challenged with LPS, and the resulting inflammatory reaction was quantified by measuring leukocyte cell infiltration in the aqueous humor and by measuring the amount of protein leakage into the aqueous humor. In the Figures, "LPS" corresponds to the control where no other topical treatment was applied. "Vehicle" corresponds to an eye drop ophthalmic vehicle solution containing no drug, and which otherwise comprises 0.1% polysorbate 80 in an aqueous medium. "Pred-Forte" corresponds to an ophthalmic solution of 1% prednisolone acetate. "Acular" corresponds to an ophthalmic solution of 0.4% ketorolac. The concentrations of cicaprost used in the ophthalmic vehicle solution were 0.001%, 0.01%, and 0.1%.

Figure 9:
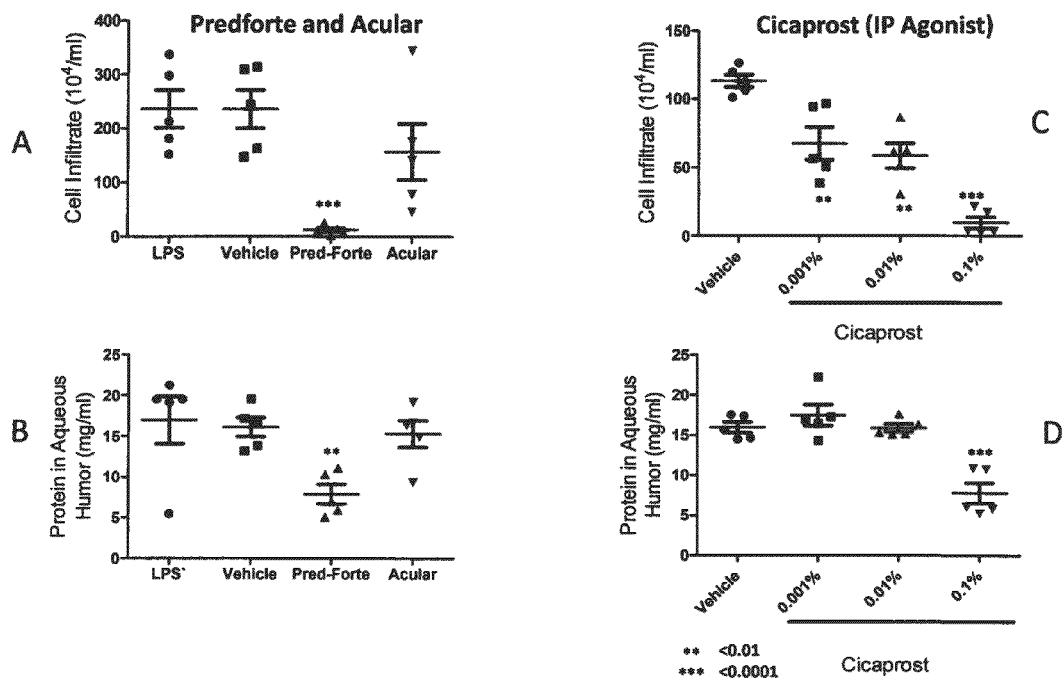
FIGS. 9A-D illustrate the effect of cicaprost in comparison to steroid treatment on cell infiltrate measurements and aqueous humor protein leakage in a rat EIU model.

As shown in FIGS. 9A-B, Pred-Forte and Acular both reduced cell infiltrate and protein in the aqueous humor compared to the LPS and Vehicle controls. Pred-Forte especially reduced cell infiltrate, while Acular showed a smaller benefit.

Turning to FIGS. 9C-D, cicaprost shows an increasing effect on lowering cell infiltrate, and 0.1% cicaprost solution reduced cell infiltrate to near-zero levels. Protein in the aqueous humor was also reduced, especially when a 0.1% cicaprost solution was used.

Cicaprost and other IP receptor agonists may be beneficial in reducing ocular inflammation. In particular, a 0.1% solution of cicaprost was shown to be effective in reducing cell infiltrate and protein leakage in the rat EIU model in comparison to the steroid Pred-Forte, and at a lower concentration of active ingredient. Further, administration of cicaprost instead of Pred-Forte avoids other side effects resulting from steroid administration.

Example 10

Figure 10:
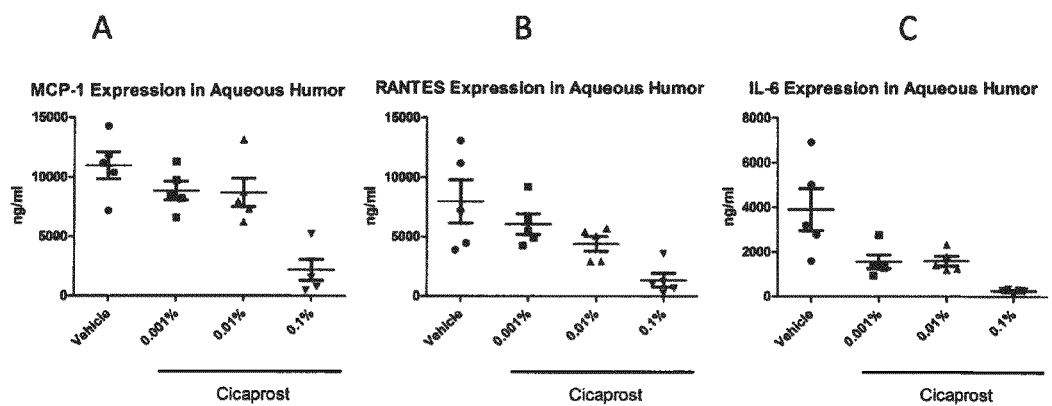
FIGS. 10A-C illustrate the effect of cicaprost on inflammatory cytokine secretion in the aqueous humor in a rat EIU model.

FIGS. 10A-C depict the results of experiments measuring cytokine expression in a rat EIU model, where the rats were challenged with LPS. Cytokine concentration (here, MCP-1, RANTES, and IL-6) was measured subsequent to the LPS challenge, after topical application of cicaprost at concentrations from 0.001%, 0.01%, and 0.1%, together with a control eye drop vehicle (abbreviated "Vehicle" in the figures) where no cicaprost was present. As shown, increasing amounts of topically-applied cicaprost reduced the concentration of the monitored cytokines MCP-1, RANTES, and IL-6 compared to the control.

Example 11

Figure 11:
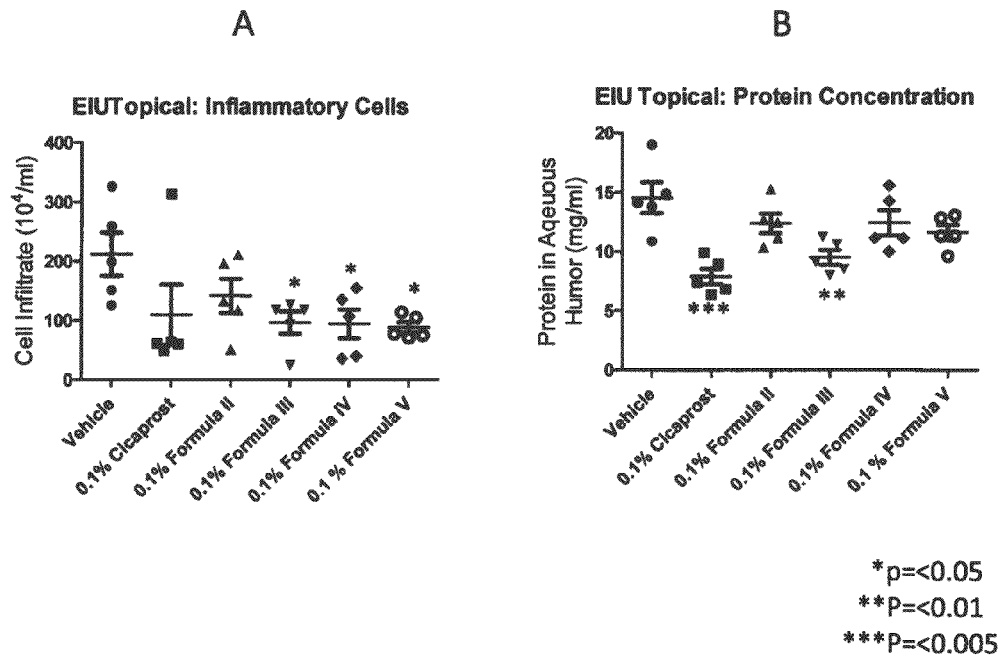
FIGS. 11A-B illustrate the effect of several cicaprost prodrugs on cell infiltrate and aqueous humor protein leakage in a rat EIU model.

FIGS. 11A-B show the results of experiments measuring cell infiltrate and protein in the aqueous humor in a rat EIU model challenged with LPS, where the rats were challenged in a similar manner as described previously. Cicaprost, as well as the cicaprost prodrugs described above in Formulas II-V, were separately topically dosed as a 0.1% ophthalmic solution. Turning to FIG. 11A, administration of either cicaprost or its prodrugs (Formulas II-V) caused a reduction in cell infiltration in comparison with the control vehicle. With respect to FIG. 11B, administration of cicaprost reduced protein concentration in the aqueous humor with respect to the control vehicle. Formula III was approximately comparable to cicaprost in effect, and reduced protein concentration in the aqueous humor to a similar extent. Formulas II, IV, and V exhibited some reduction in protein concentration with respect to the control vehicle, although to a lesser extent than cicaprost and Formula III.

Example 12

The effect of cicaprost on corneal wound healing was evaluated in an anterior segment model using 3 pairs of donated human eyes. Wounding (anterior keratectomy, AK) was induced by scoring the cornea in 8 mm diameter, and the epithelium was removed using a gill knife. The anterior segment of the eye was dissected and cultured in complete medium on a rotating platform for several days to maintain tissue differentiation. Two drops (approximately 50 µl per drop) of 0.1% cicaprost were dosed at 0 and 9 hours on one eye ("Cp"), while the other eye ("CN") was treated with vehicle (0.1% polysorbate 80 in saline). The initial wound and the progression of wound closure was visualized with 0.015% fluorescein, and the wound area recorded at 0 and 18 hours, as shown in FIG. 12.

Figure 12:
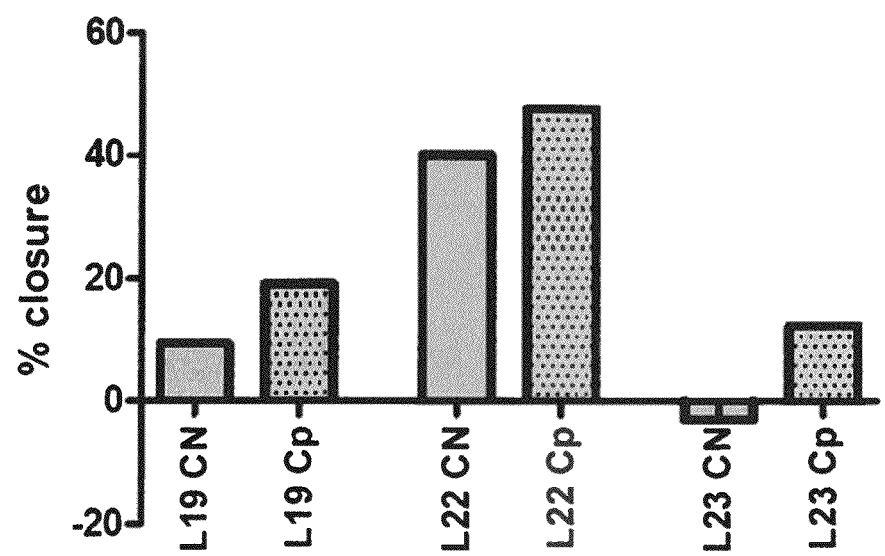
FIG. 12 illustrates the effect of cicaprost on a corneal wound closure model.

With reference to FIG. 12, the three pairs of donor eyes are denoted as L19, L22, and L23, respectively. In comparison to the control eyes dosed with vehicle ("CN"), the eyes dosed with cicaprost ("Cp") showed an improvement in the percentage of wound closure at 18 hours. All of the tested eyes showed an increase in the percentage of wound closure in comparison to the untreated eyes.

Those skilled in the art will appreciate that numerous changes and modifications can be made to the preferred embodiments of the invention as described herein, and that such changes and modifications can be made without departing from the spirit of the invention and without limiting the overall scope hereof.

The invention claimed is:

1. A method of promoting wound healing, comprising administering cicaprost to an eye, wherein the cicaprost is present at a concentration of about 0.1%.

2. The method of claim 1, wherein the wound healing is corneal wound healing.

\* \* \* \* \*